(12) United States Patent
Shelton, IV et al.

(10) Patent No.: US 7,367,485 B2
(45) Date of Patent: *May 6, 2008

(54) SURGICAL STAPLING INSTRUMENT INCORPORATING A MULTISTROKE FIRING MECHANISM HAVING A ROTARY TRANSMISSION

(75) Inventors: Frederick E. Shelton, IV, Hillsboro, OH (US); Michael Earl Setser, Burlington, KY (US); Douglas B. Hoffman, Harrison, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 654 days.

This patent is subject to a terminal disclaimer.

(21) Appl. No.: 10/881,105

(22) Filed: Jun. 30, 2004

(65) Prior Publication Data

US 2006/0000868 A1    Jan. 5, 2006

(51) Int. Cl.
*A61B 17/068* (2006.01)
(52) U.S. Cl. .................. 227/175.2; 227/19; 227/176.1; 227/180.1
(58) Field of Classification Search .................. 227/19, 227/176.1, 175.2, 180.1, 175.1, 178.1
See application file for complete search history.

(56) References Cited

U.S. PATENT DOCUMENTS

| | | | |
|---|---|---|---|
| 2,883,984 A * | 4/1959 | Candido, Jr. et al. ......... | 604/61 |
| 3,269,630 A | 8/1966 | Fleischer | |
| 3,837,555 A | 9/1974 | Green | |
| 3,949,924 A | 4/1976 | Green | |
| 4,527,724 A * | 7/1985 | Chow et al. .................... | 227/8 |
| 4,580,712 A | 4/1986 | Green | |
| 4,606,343 A | 8/1986 | Conta et al. | |
| 4,796,793 A * | 1/1989 | Smith et al. .................. | 227/19 |
| 4,869,415 A | 9/1989 | Fox | |
| 4,976,686 A * | 12/1990 | Ball et al. ..................... | 604/61 |
| 5,465,895 A | 11/1995 | Knodel | |
| 5,487,500 A * | 1/1996 | Knodel et al. ........... | 227/181.1 |
| 5,706,997 A * | 1/1998 | Green et al. ............. | 227/175.2 |
| 5,762,255 A | 6/1998 | Chrisman | |
| 5,762,256 A | 6/1998 | Mastri et al. | |
| 5,782,396 A | 7/1998 | Mastri et al. | |
| 5,826,776 A * | 10/1998 | Schulze et al. .......... | 227/176.1 |
| 5,855,311 A * | 1/1999 | Hamblin et al. ......... | 227/176.1 |
| 5,865,361 A | 2/1999 | Milliman et al. | |
| 6,032,849 A | 3/2000 | Mastri et al. | |
| 6,079,606 A | 6/2000 | Milliman et al. | |
| 6,241,139 B1 | 6/2001 | Milliman et al. | |
| 6,330,965 B1 | 12/2001 | Milliman et al. | |
| 6,582,452 B2 * | 6/2003 | Coleman et al. ............ | 606/213 |
| 6,986,451 B1 * | 1/2006 | Mastri et al. ............. | 227/176.1 |
| 7,059,508 B2 * | 6/2006 | Shelton et al. ........... | 227/175.2 |
| 7,128,254 B2 * | 10/2006 | Shelton et al. ........... | 227/181.1 |

(Continued)

FOREIGN PATENT DOCUMENTS

EP        0 070 230        6/1981

(Continued)

*Primary Examiner*—Scott A. Smith
(74) *Attorney, Agent, or Firm*—Frost Brown Todd, LLC

(57) ABSTRACT

A surgical stapling and severing instrument particularly suited to endoscopic procedures incorporates a handle that produces separate closing and firing motions to actuate an end effector. In particular, the handle produces multiple firing strokes in order to reduce the required amount of force required to fire (i.e., staple and sever) the end effector.

15 Claims, 12 Drawing Sheets

U.S. PATENT DOCUMENTS

2002/0117533 A1   8/2002    Milliman et al.
2004/0232195 A1  11/2004   Shelton et al.
2004/0232196 A1  11/2004   Shelton et al.
2004/0232197 A1  11/2004   Shelton et al.
2004/0232199 A1  11/2004   Shelton et al.
2004/0232200 A1  11/2004   Shelton et al.

FOREIGN PATENT DOCUMENTS

EP      0 748 614      12/1996
EP      1 402 821      3/2004
EP      05254067.1     9/2005
WO      WO 99 15086    4/1999

\* cited by examiner

SURGICAL STAPLING INSTRUMENT INCORPORATING A MULTISTROKE FIRING MECHANISM HAVING A ROTARY TRANSMISSION

FIELD OF THE INVENTION

The present invention relates in general to surgical stapler instruments that are capable of applying lines of staples to tissue while cutting the tissue between those staple lines and, more particularly, to improvements relating to stapler instruments and improvements in processes for forming various components of such stapler instruments that accomplish firing with multiple strokes of a trigger.

BACKGROUND OF THE INVENTION

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

An example of a surgical stapler suitable for endoscopic applications is described in U.S. Pat. No. 5,465,895, which advantageously provides distinct closing and firing actions. Thereby, a clinician is able to close the jaw members upon tissue to position the tissue prior to firing. Once the clinician has determined that the jaw members are properly gripping tissue, the clinician can then fire the surgical stapler with a single firing stroke, thereby severing and stapling the tissue. The simultaneous severing and stapling avoids complications that may arise when performing such actions sequentially with different surgical tools that respectively only sever or staple.

One specific advantage of being able to close upon tissue before firing is that the clinician is able to verify via an endoscope that a desired location for the cut has been achieved, including a sufficient amount of tissue has been captured between the opposing jaws. Otherwise, opposing jaws may be drawn too close together, especially pinching at their distal ends, and thus not effectively forming closed staples in the severed tissue. At the other extreme, an excessive amount of clamped tissue may cause binding and an incomplete firing.

Generally, a single closing stroke followed by a single firing stroke is a convenient and efficient way to perform severing and stapling. However, in some instances, it would be desirable for multiple firing strokes to be required. For example, surgeons are able to select, from a range of jaw sizes, a corresponding length of staple cartridge for the desired length of cut. Longer staple cartridges require a longer firing stroke. Thus, a hand-squeezed trigger to effect the firing is required to exert a larger force for these longer staple cartridges in order to sever more tissue and drive more staples as compared to a shorter staple cartridge. It would be desirable for the amount of force to be lower and comparable to shorter cartridges so as not to exceed the hand strength of some surgeons. In addition, some surgeons not familiar with the larger staple cartridges may become concerned that binding or other malfunction has occurred when an unexpectedly higher force is required.

One approach to lower the required force for a firing stroke is a ratcheting mechanism that allows a firing trigger to be stroked multiple times, as described in U.S. Pat. Nos. 5,762,256 and 6,330,965. However, it is believed that the conversion of the reciprocating motion of the firing trigger directly into a solid rack by a pawl constrains design options for a desired amount of firing motion during each firing stroke. In addition, these known surgical stapling instruments with multiple-stroke firing mechanisms do not have the advantages of a separate closure and firing action.

Consequently, a significant need exists for a surgical stapling instrument that uses multiple firing strokes to achieve a desired length of severing and stapling with a desired relationship of firing stroke travel to longitudinal firing motion produced for an end effector.

BRIEF SUMMARY OF THE INVENTION

The invention overcomes the above-noted and other deficiencies of the prior art by providing a surgical stapling and severing instrument having a rotary transmission that transfers a sequence of multiple firing strokes while preventing backup of a firing member. Thereby, an end effector of the instrument requiring increased firing forces and/or increased firing travel may be readily fired with a multiple stroke firing trigger. Yet, the instrument has a separate closure capability that allows a surgeon to position tissue without necessarily firing the end effector.

In one aspect of the invention, a surgical instrument has an end effector that is responsive to a longitudinal firing motion to perform a surgical operation. A user causes movement in a firing actuator to create the firing motion that is selectively transferred by a firing mechanism. Specifically, a cam disk has a plurality of cam lobes about at least a portion of its circumference that are respectively engaged by a drive wedge coupled to the firing actuator when making a firing motion. The cam disk is coupled to a rack by gear engagement to translate this intermittent rotational motion into the longitudinal firing motion.

In another aspect of the invention, a surgical instrument has an end effector that severs and staples tissue. In particular, a staple applying assembly distal has an anvil having a staple forming surface moveable from an open position spaced away from a plurality of staples to a closed position adjacent to the plurality of staples. A staple applying mechanism has a rotary cam member with at least one cam lobe associated with at least one coupling member such that rotation of the rotary cam member causes the application of at least a portion of the staples from the staple applying assembly. Thereby, a multiple stroke firing may be used to sever and staple tissue.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
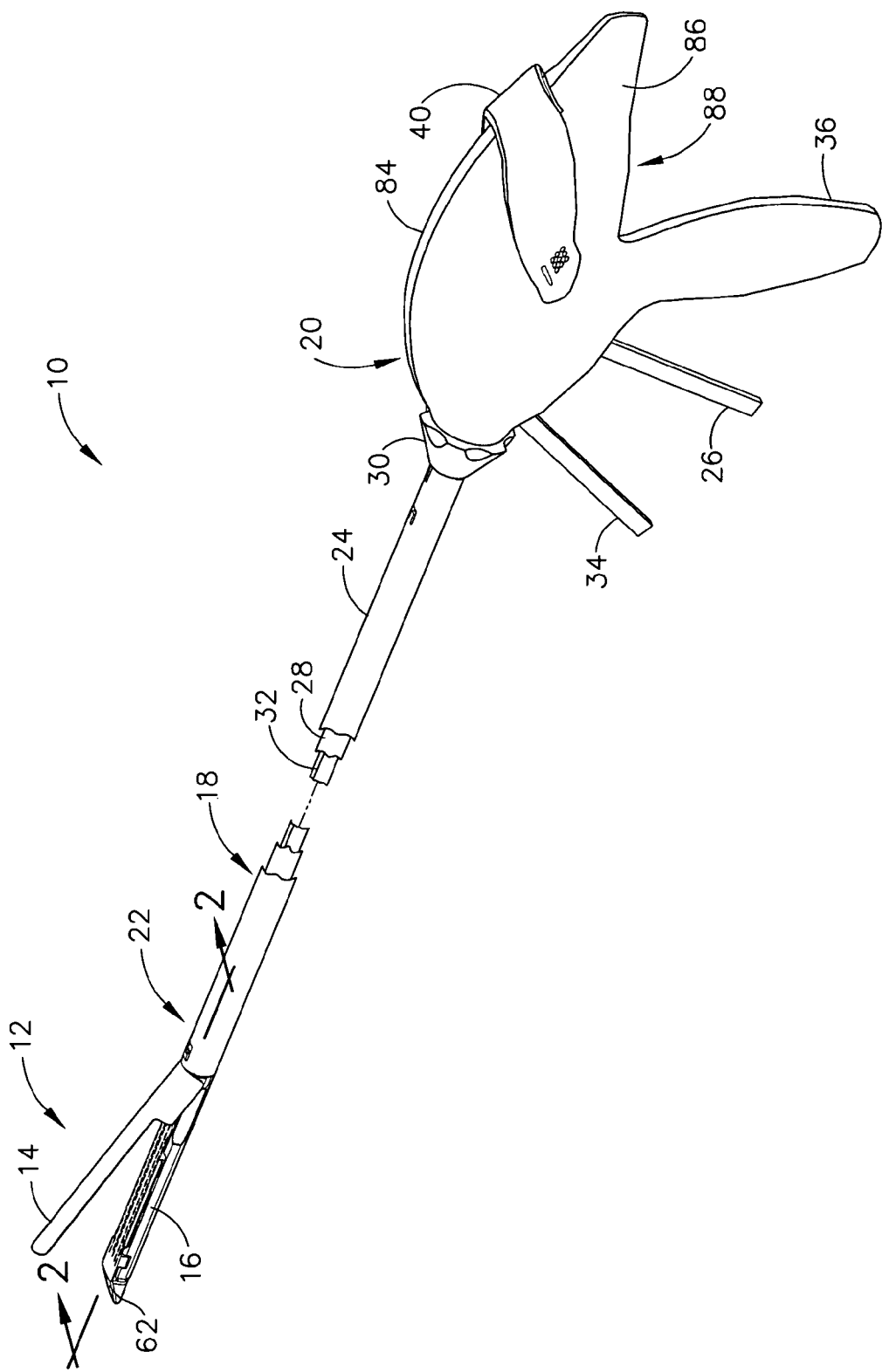
FIG. 1 is a perspective view of a surgical stapling and severing instrument having an open end effector.
Figure 2:
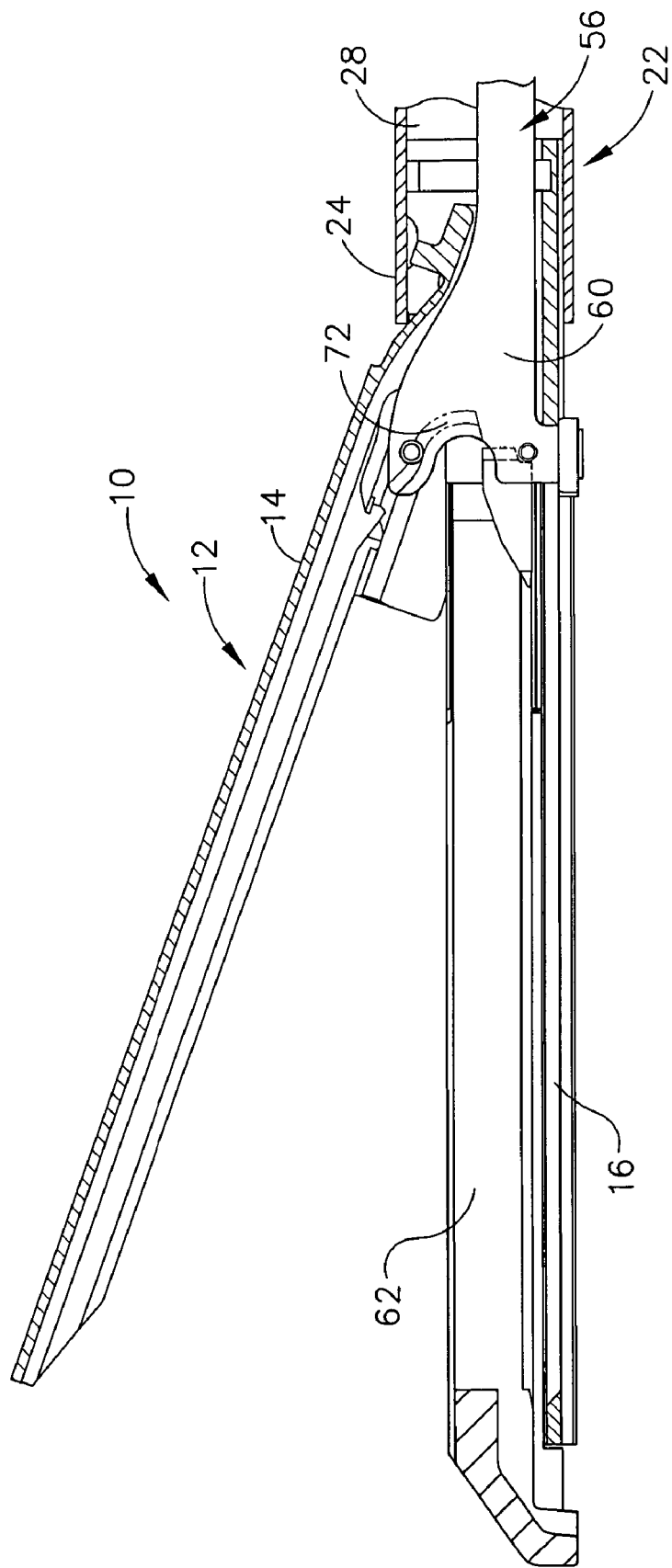
FIG. 2 is a left side elevation view in cross section along lines 2-2 of the open end effector of FIG. 1.

Turning to the Drawings, wherein like numerals denote like components throughout the several views, FIGS. 1-4 depict a surgical stapling and severing instrument 10 that is capable of practicing the unique benefits of the present invention. The surgical stapling and severing instrument 10 incorporates an end effector 12 having an anvil 14 pivotally attached to an elongate channel 16, forming opposing jaws for clamping tissue to be severed and stapled. The end effector 12 is coupled by a shaft 18 to a handle 20. An implement portion 22, formed by the end effector 12 and shaft 18, is advantageously sized for insertion through a trocar or small laparoscopic opening to perform an endoscopic surgical procedure while being controlled by a surgeon grasping the handle 20. The handle 20 advantageously includes features that allow separate closure motion of the end effector 12 from firing, as well as enabling multiple firing strokes to effect firing (i.e., severing and stapling) of the end effector 12 while indicating the degree of firing to the surgeon.

To these ends, a closure tube 24 of the shaft 18 is coupled between a closure trigger 26 and the anvil 14 to cause closure of the end effector 12. Within the closure tube 24, a frame 28 is coupled between the elongate channel 16 and the handle 20 to longitudinally position and support the end effector 12. A rotation knob 30 is coupled with the frame 28, and both elements are rotatably coupled to the handle 20 with respect to a rotational movement about a longitudinal axis of the shaft 18. Thus, the surgeon can rotate the end effector 12 by turning the rotation knob 30. The closure tube 24 is also rotated by the rotation knob 30 but retains a degree of longitudinal movement relative thereto to cause the closure of the end effector 12. Within the frame 28, a firing rod 32 is positioned for longitudinal movement and coupled between the anvil 14 of the end effector 12 and a multiple-stroke firing trigger 34. The closure trigger 26 is distal to a pistol grip 36 of the handle 20 with the firing trigger 34 distal to both the pistol grip 36 and closure trigger 26.

In endoscopic operation, once the implement portion 22 is inserted into a patient to access a surgical site, a surgeon refers to an endoscopic or other diagnostic imaging device to position tissue between the anvil 14 and elongate channel 16. Grasping the closure trigger 26 and pistol grip 36, the surgeon may repeatedly grasp and position the tissue. Once satisfied as to the location of the tissue relative to the end effector 12 and the amount of tissue therein, the surgeon depresses the closure trigger 26 fully toward the pistol grip 36, clamping the tissue in the end effector 12 and locking the closure trigger 26 in this clamped (closed) position. If not satisfied with this position, the surgeon may release the closure trigger 26 by depressing a release button 38 (FIG. 4), whose operation is described more fully below, and thereafter repeat the procedure to clamp tissue.

If clamping is correct, the surgeon may proceed with firing the surgical stapling and severing instrument 10. Specifically, the surgeon grasps the firing trigger 34 and pistol grip 36, depressing the firing trigger 34 a predetermined number of times. The number of firing strokes necessary is ergonomically determined based on a maximum hand size, maximum amount of force to be imparted to the instrument during each firing stroke, and the longitudinal distance and force needed to be transferred through the firing rod 32 to the end effector 12 during firing. As will be appreciated in the discussion below, individual surgeons may choose to cycle the firing trigger 34 a different angular range of motion, and thus increase or decrease the number of firing strokes.

In FIG. 1, after firing the surgical stapling and severing instrument 10, a closure release lever 40 is activated to retract the firing mechanism. Depressing the closure release lever 40 disengages a rotary transmission firing mechanism 42 within the handle 20, enabling a spring 172 to retract the firing rod 32 from the end effector 12.

Implement Portion Including an E-Beam End Effector.

The advantages of a handle 20 capable of providing multiple-stroke firing motion has application to a number of instruments, with one such end effector 12 being depicted in FIGS. 1-4. The anvil 14 of end effector 12 responds to the closure motion from the handle 20 that is transferred longitudinally and distally by the closure tube 24. The elongate channel 16 slidingly engages the translating and closing anvil 14 to form opposing jaws, and the frame 28 fixedly engages the stationary channel 16 to form a rigid attachment to the handle 20. The closure tube 24 engages the anvil 14 distal to the pin in slot connection between the anvil 14 and elongate channel 16. Thus, a distal movement of the closure tube 24 relative to the frame 28 effects closure and a proximal movement relative to the frame 28 effects opening of the end effector 12.

Figure 4:
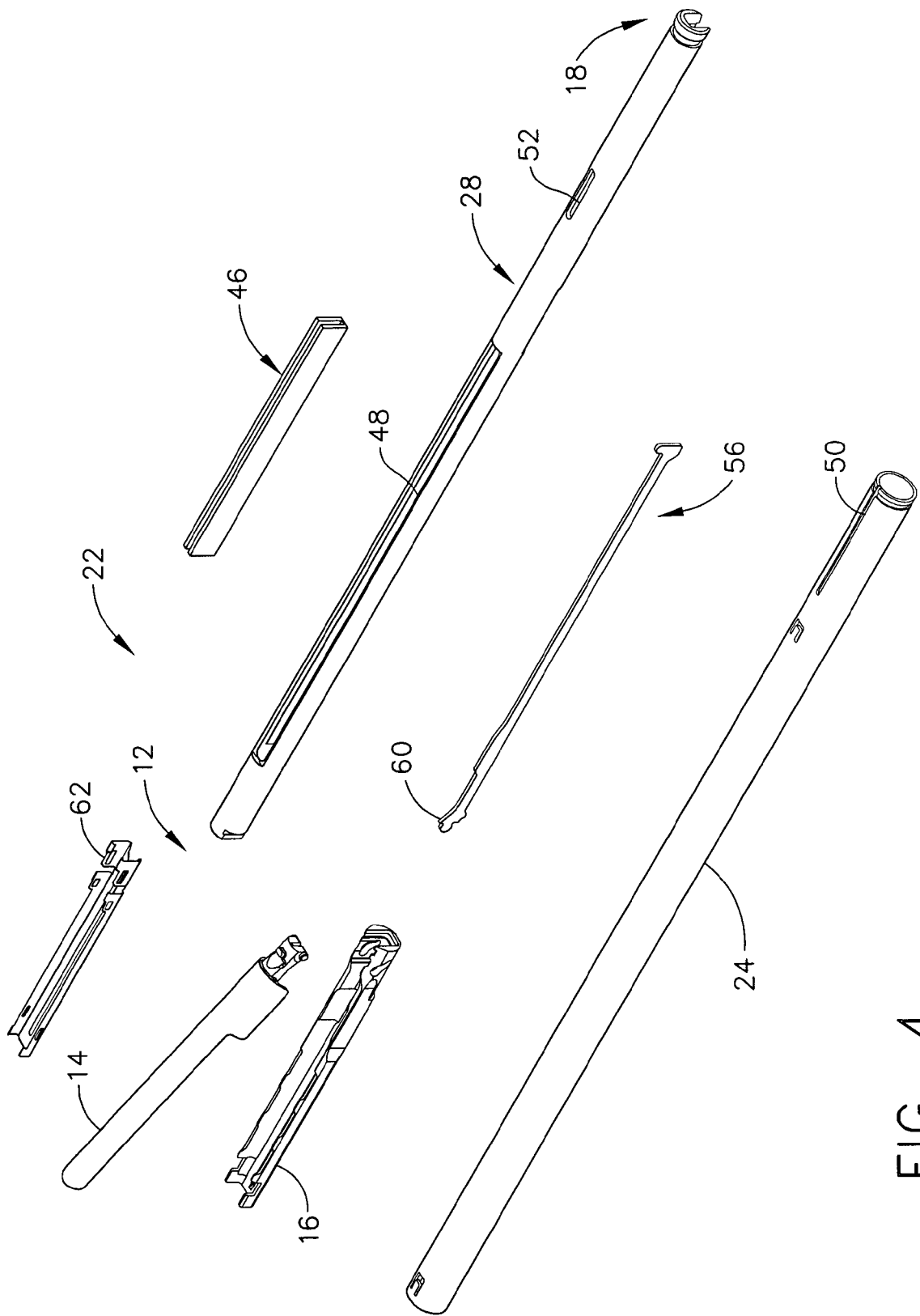
FIG. 4 is an exploded, perspective view of an implement portion of the surgical stapling and severing instrument of FIG. 1.

With particular reference to FIG. 4, the implement portion 22 also includes components that respond to a firing motion from the handle 20, specifically of the firing rod 32 (not shown in FIG. 4) that couples a longitudinal motion between the firing mechanism 42 in the handle 20 and the implement portion 22. In particular, the firing rod 32 (shown disassembled in FIG. 5) rotatably engages a firing trough member 46 slidably located within a longitudinal recess 48 in frame 28. Firing trough member 46 moves longitudinally within frame 28 in direct response to longitudinal motion of firing rod 32. A longitudinal slot 50 in the closure tube 24 operably couples with the rotation knob 30 (not shown), the longitudinal slot 50 further allowing the rotation knob 30 to engage the frame 28 at a small longitudinal slot 52 therein to effect rotation. A tab is located in front of slot 50 on the closure tube 24 and the tab is bent down into slot 52 in the frame 28 to couple the closure tube 24 to the frame 28. The length of the longitudinal slot 50 in the closure tube 24 is sufficiently long as to allow relative longitudinal motion with the rotation knob 30 to accomplish closure motions respectively.

Figure 3:
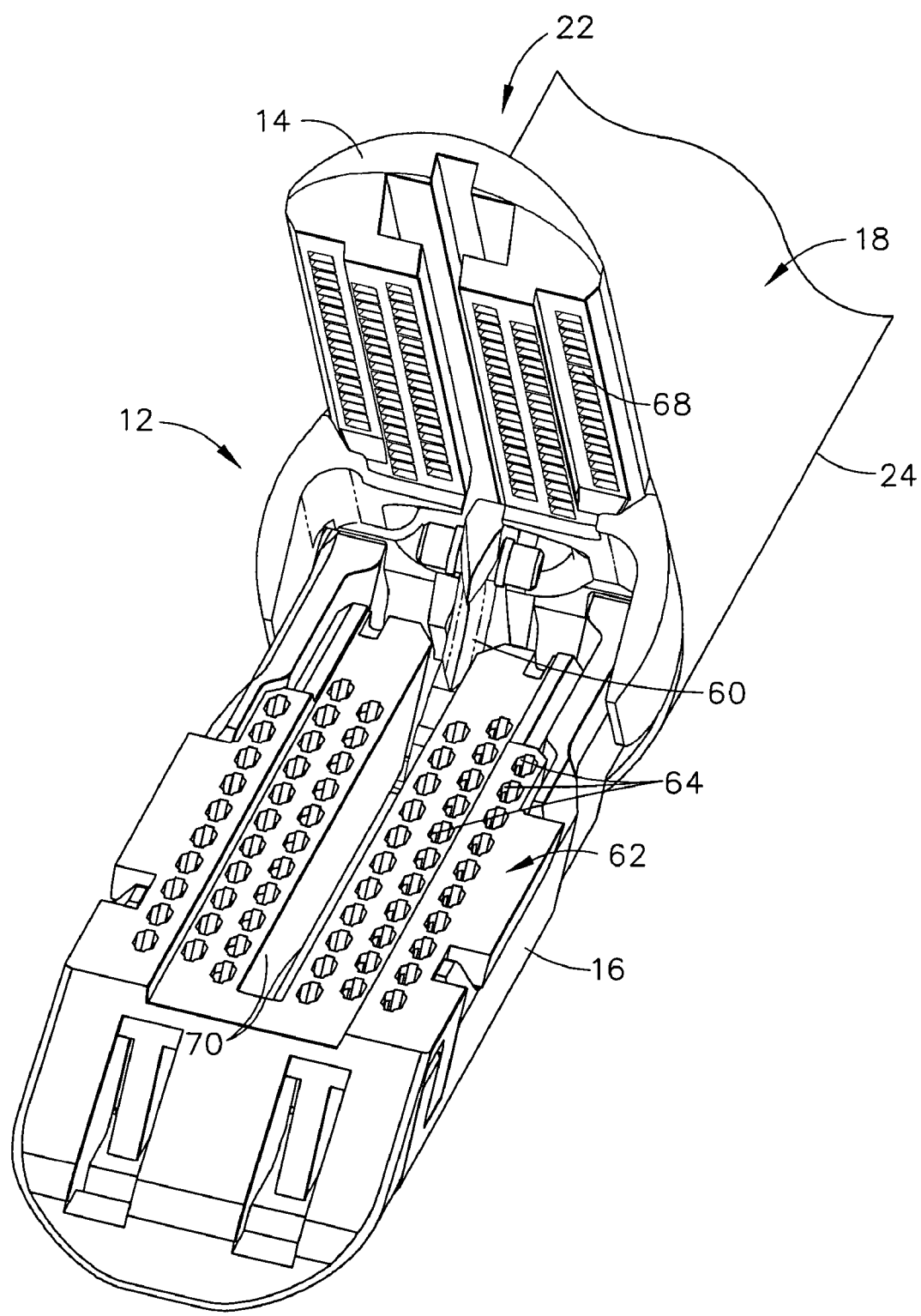
FIG. 3 is a perspective view of the open end effector of FIG. 1.

The distal end of the frame trough member 46 is attached to a proximal end of a firing bar 56 that moves with the frame 28, to distally project an E-beam 60 into the end effector 12. The end effector 12 includes a staple cartridge 62 that is actuated by the E-beam 60 that causes staples to be drive up from staple apertures 64 of the cartridge 62 into contact with staple forming grooves 68 of the anvil 14, creating formed "B" shaped staples. With particular reference to FIG. 3, the staple cartridge body 86 further includes a proximally open, vertical slot 70 for passage of a vertically oriented cutting surface provided along a distal end of E-beam 60 to cut tissue while being stapled.

The illustrative end effector 12 is described in greater detail in five co-pending and commonly-owned U.S. patent applications, the disclosure of each being hereby incorporated by reference in their entirety: (1) "SURGICAL STAPLING INSTRUMENT HAVING A SINGLE LOCKOUT MECHANISM FOR PREVENTION OF FIRING", Ser. No. 10/441,424, to Frederick E. Shelton, Mike Setser, Bruce Weisenburgh, filed 20 Jun. 2003; (2) "SURGICAL STAPLING INSTRUMENT HAVING SEPARATE DISTINCT CLOSING AND FIRING SYSTEMS", Ser. No. 10/441,632, to Frederick E. Shelton, Mike Setser, Brian J. Hemmelgarn, filed 20 Jun. 2003; (3) "SURGICAL STAPLING INSTRUMENT HAVING A SPENT CARTRIDGE LOCKOUT", Ser. No. 10/441,565, to Frederick E. Shelton, Mike Setser, Bruce Weisenburgh, filed 20 Jun. 2003; (4) "SURGICAL STAPLING INSTRUMENT HAVING A FIRING LOCKOUT FOR AN UNCLOSED ANVIL", Ser. No. 10/441,580, to Frederick E. Shelton, Mike Setser, Bruce Weisenburgh, filed 20 Jun. 2003; and (5) "SURGICAL STAPLING INSTRUMENT INCORPORATING AN E-BEAM FIRING MECHANISM", Ser. No. 10/443,617, to Frederick E. Shelton, Mike Setser, Bruce Weisenburgh, filed 20 Jun. 2003.

It should be appreciated that although a nonarticulating shaft 18 is illustrated herein, applications of the present invention may include instruments capable of articulation, such as described in five co-pending and commonly owned U.S. patent applications, the disclosure of each being hereby incorporated by reference in their entirety: (1) "SURGICAL INSTRUMENT INCORPORATING AN ARTICULATION MECHANISM HAVING ROTATION ABOUT THE LONGITUDINAL AXIS", Ser. No. 10/615,973, to Frederick E. Shelton, Brian J. Hemmelgarn, Jeff Swayze, Kenneth S. Wales, filed 9 Jul. 2003; (2) "SURGICAL STAPLING INSTRUMENT INCORPORATING AN ARTICULATION JOINT FOR A FIRING BAR TRACK", Ser. No. 10/615,962, to Brian J. Hemmelgarn, filed 9 Jul. 2003; (3) "A SURGICAL INSTRUMENT WITH A LATERAL-MOVING ARTICULATION CONTROL", Ser. No. 10/615,972, to Jeff Swayze, filed 9 Jul. 2003; (4) "SURGICAL STAPLING INSTRUMENT INCORPORATING A TAPERED FIRING BAR FOR INCREASED FLEXIBILITY AROUND THE ARTICULATION JOINT", Ser. No. 10/615,974, to Frederick E. Shelton, Mike Setser, Bruce Weisenburgh, filed 9 Jul. 2003; and (5) "SURGICAL STAPLING INSTRUMENT HAVING ARTICULATION JOINT SUPPORT PLATES FOR SUPPORTING A FIRING BAR", Ser. No. 10/615,971, to Jeff Swayze, Joseph Charles Hueil, filed 9 Jul. 2003.

Multi-Stroke Firing Handle.

In FIGS. 5-8, the handle 20 responds to actuation of the closure trigger 26 and firing trigger 34 to generate respectively the closure and firing motions to the implement portion 22. With regard to the closure motion, the closure trigger 26 includes an upper portion 76 that includes three lateral apertures, a forwardly positioned pin hole 78, a lower, aft pivot hole 80, and a center cutout 82. Three rods laterally oriented between and engaged to right and left half shells 84, 86 of a handle housing 88 (with the right half shell 84 shown in FIGS. 5-6 and the left half shell 86 shown in FIG. 7). In particular, an aft rod 90 passes through the aft pivot hole 84 of the upper portion 80 of the closure trigger 26, and thus the closure trigger 26 pivots about the aft rod 90. A front rod 92, which is distally positioned to the aft rod 90, and a top rod 94, which is above the front rod 92, pass through the center cutout 86, which is shaped to constrain movement of the closure trigger 26 by contacting the front and top rods 92, 94 at each extreme of trigger travel. Thus, the center cutout 86 includes a vertical portion, whose bottom surface contacts the front rod 92 when the closure trigger 26 is forward (distal), and includes an upper, proximally sloped portion, whose top and forward surfaces contact the top rod 94 respectively when the closure trigger 26 is at its forward, relaxed position and its proximal, actuated position.

A closure yoke 96, which engages the closure tube 24, is longitudinally slidingly received within the handle housing 92 and is engaged at its distal end to a proximal end of the closure tube 24, thus transferring longitudinal closure motion to the closure tube 24 and hence to the anvil 14 for closing the end effector 12. This engagement allows rotation of the closure tube 24 while the closure yoke 96 does not rotate. Above this engagement, a lateral pin hole 100 is coupled to a closure link 102 by a front pin 104, with the other end of the closure link 102 coupled to the pin hole 82 of the closure trigger 26 via an aft pin 106.

A triangular spacer 120 includes holes 122, 124, 126 to receive the rods 90, 92, 94 respectively and is sandwiched between a cam disk 130 and the upper portion 80 of the closure trigger 26. Cam disk 130 rotates about the front rod 92 and includes a semi-circular slot 132 that receives the aft and top rods 90, 94. A central hole 134 receives front rod 92. To the left of the cam disk 130, a rod hole 136 at an upper end 138 of the firing trigger 34 receives the top rod 94. Firing trigger 34 rotatably mounts onto rod 94 to sandwich cam disk 130 between the triangular spacer 120 and firing trigger 34. A distally opened recess 140 in the firing trigger 34 below the rod hole 136 is registered to receive the front rod 92, allowing the firing trigger 34 to be drawn distally during firing. Actuation of the closure trigger 26 swings the cam link 102 downward into contact with drive wedge pin 184 extending inwardly from firing trigger 34 causing the firing trigger 34 to be partially drawn distally and staging the firing trigger 34 for grasping.

Figure 5:
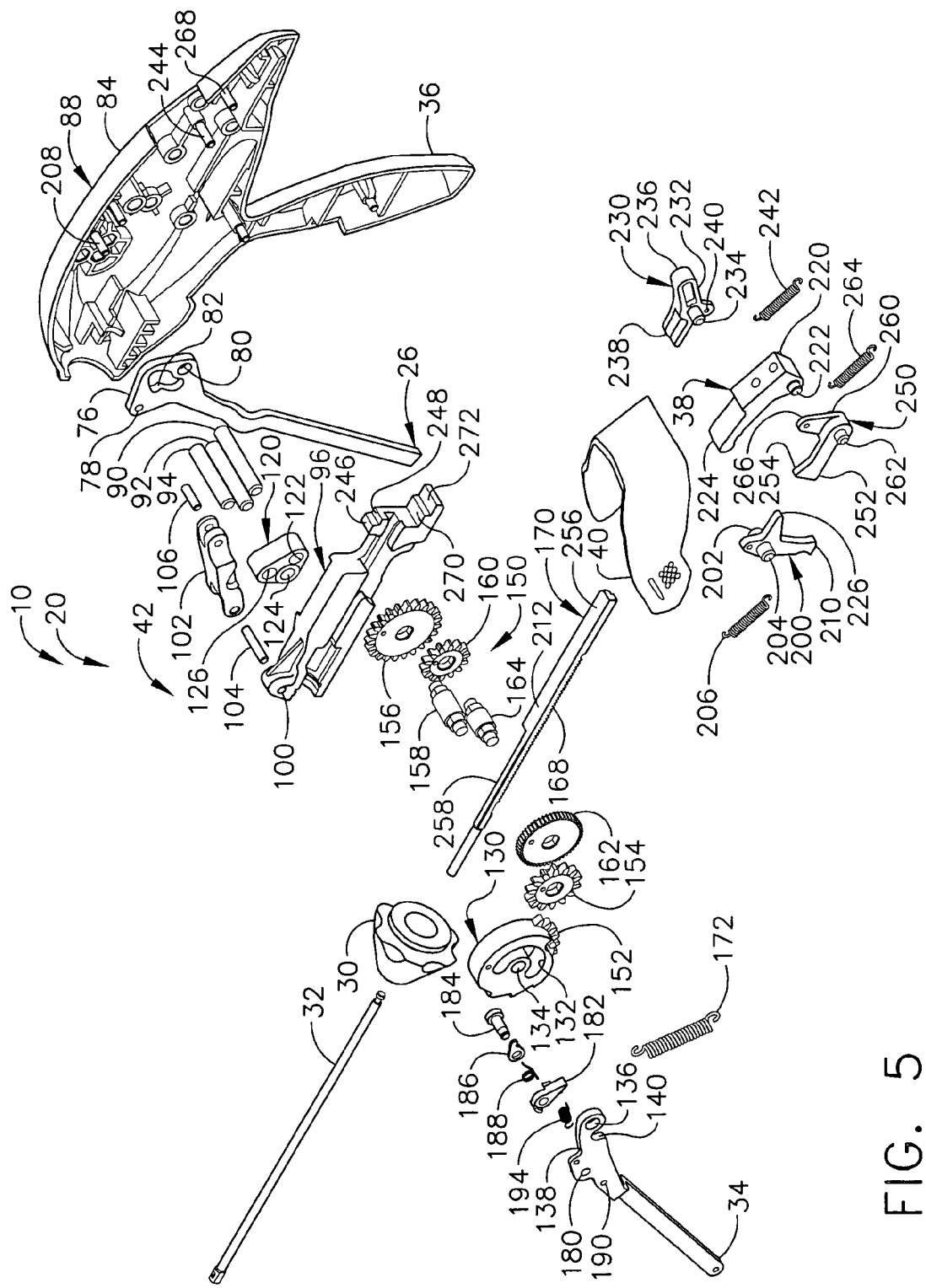
FIG. 5 is an exploded, perspective view of a handle of the surgical stapling and severing instrument of FIG. 1.
Figure 9:
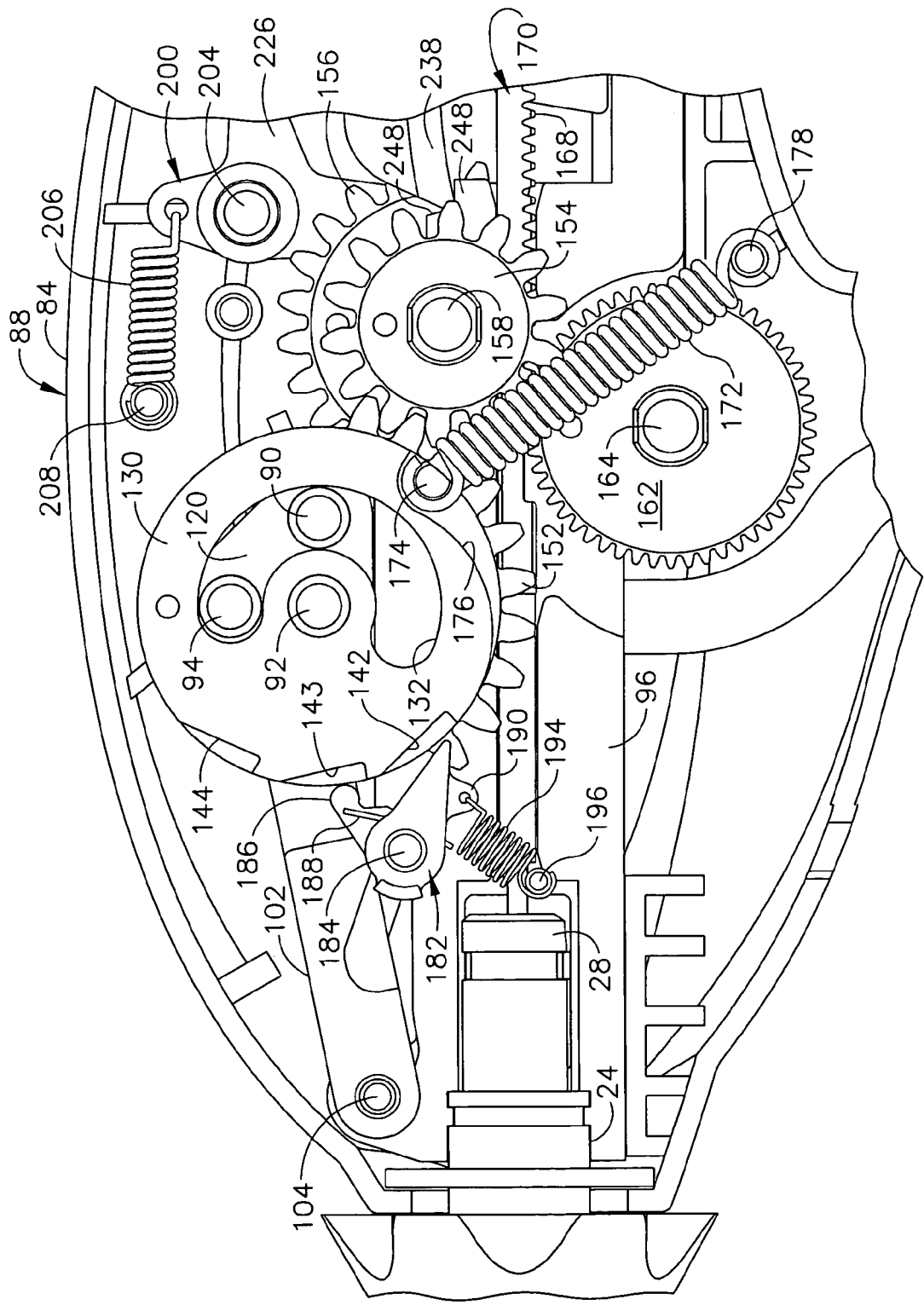
FIG. 9 is a side elevation view of the handle of FIG. 6 with the closure trigger closed and the firing trigger omitted to expose a firing drive wedge and cam lobes in a cam disk.
Figure 10:
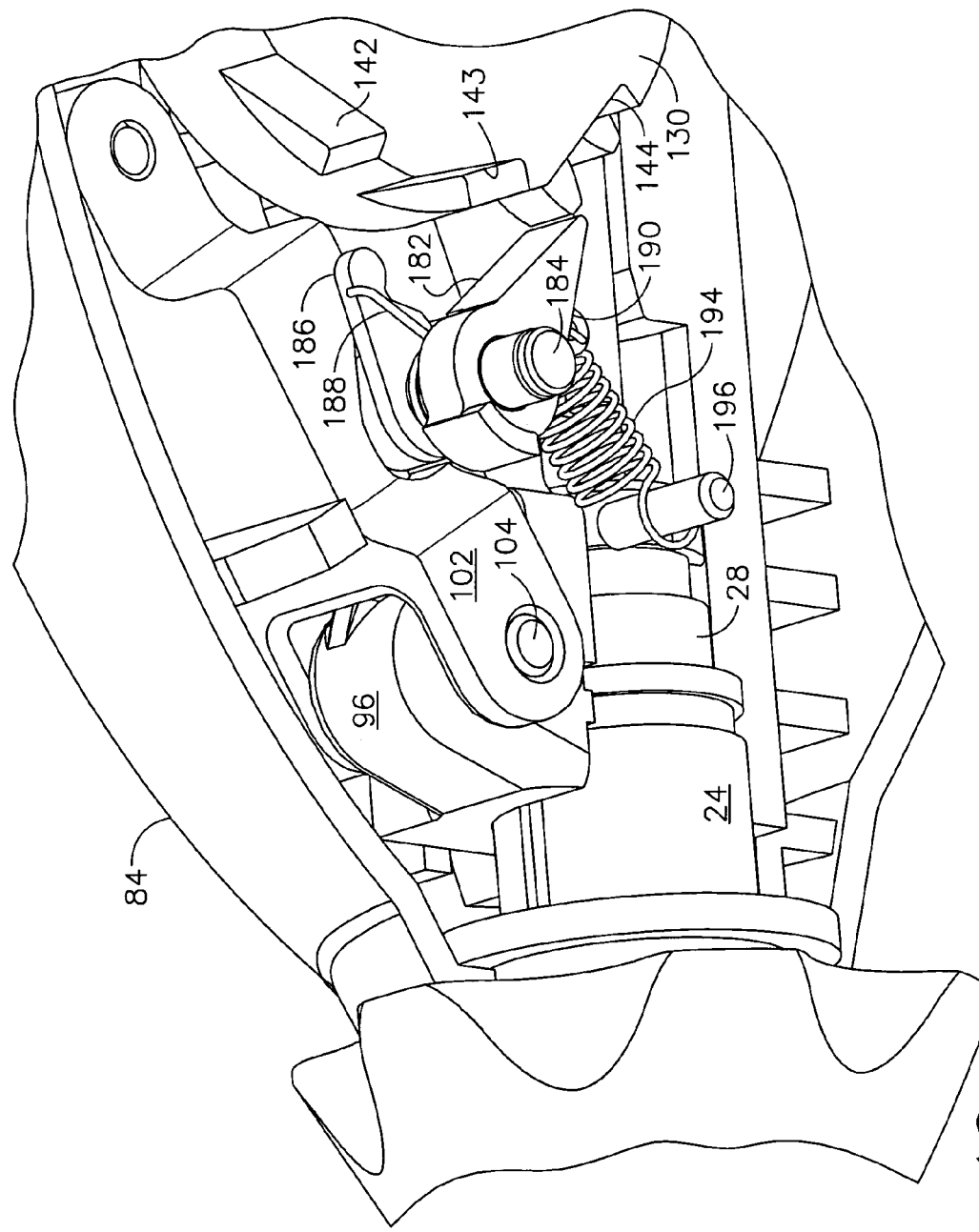
FIG. 10 is a downward perspective view of the firing drive wedge and cam lobes of FIG. 9.

With particular reference to FIGS. 5, 9, and 10, the cam disk 130 presents a series of cam lobes 142-144 (FIG. 9) about the forward portion (when in its unfired state as depicted), specifically along its left side, that are respectively engaged by the firing trigger 34 to impart a top-to-front (counter-clockwise as viewed from the left) rotation to the cam disk 130. This rotation is transferred through a gear train 150 (FIGS. 5 and 11) of the rotary transmission firing mechanism 42, beginning with a gear portion 152 about a lower portion of the right side of the cam disk 120 that engages a small idler gear 154, which thus rotates top to the rear (clockwise) at an increased rate relative to the cam disk 130. A large idler gear 156 is connected by an idler axle 158 to the small idler gear 154 and thus rotates in the same direction and rate. A second small gear 160 is enmeshed to the larger idler gear 156, and is thus rotated top to the front (counter-clockwise as viewed from the left) at a greater rate. A fine-toothed large gear 162 is connected by a second axle 164 to the second small gear 160 and thus rotates in the same direction and rate as the second small gear 160. The gear train 150 thus amplifies the motion of the cam disk 120 by including a double gear reduction feature to provide additional longitudinal firing motion. The fine-toothed large gear 162 engages a gear segment 168 on an underside of a solid rack 170 whose distal end engages the proximal end of the firing rod 32. The rack 170 has its distal portion longitudinally slidingly received within the closure yoke 96 and its proximal portion longitudinally slidingly received between right and left shell halves 84, 86 of the handle housing 88.

The selective engagement of the firing trigger 34 to the cam lobes 142-144 provides further longitudinal travel by enabling multiple firing strokes of the firing trigger 34. To prepare the gear train 150 for firing, the cam disk 130 is urged clockwise toward its unfired position by a gear train retraction spring 172 attached to a leftward projecting integral pin 174 formed within an annular recess 176 at a lower proximal edge of the cam disk 120 (FIGS. 9-10). The gear train retraction spring 172 has its other end attached to a pin 178 integral to the handle housing 88. Activation of the firing trigger 34 rotates cam disk 130 counter-clockwise to elongate the retraction spring 172. Continued actuation of the firing trigger 34 wraps the elongated retraction spring 172 about the outer diameter of the cam disk 130 as it rotates and into the annular recess 176 (not shown).

Figure 11:
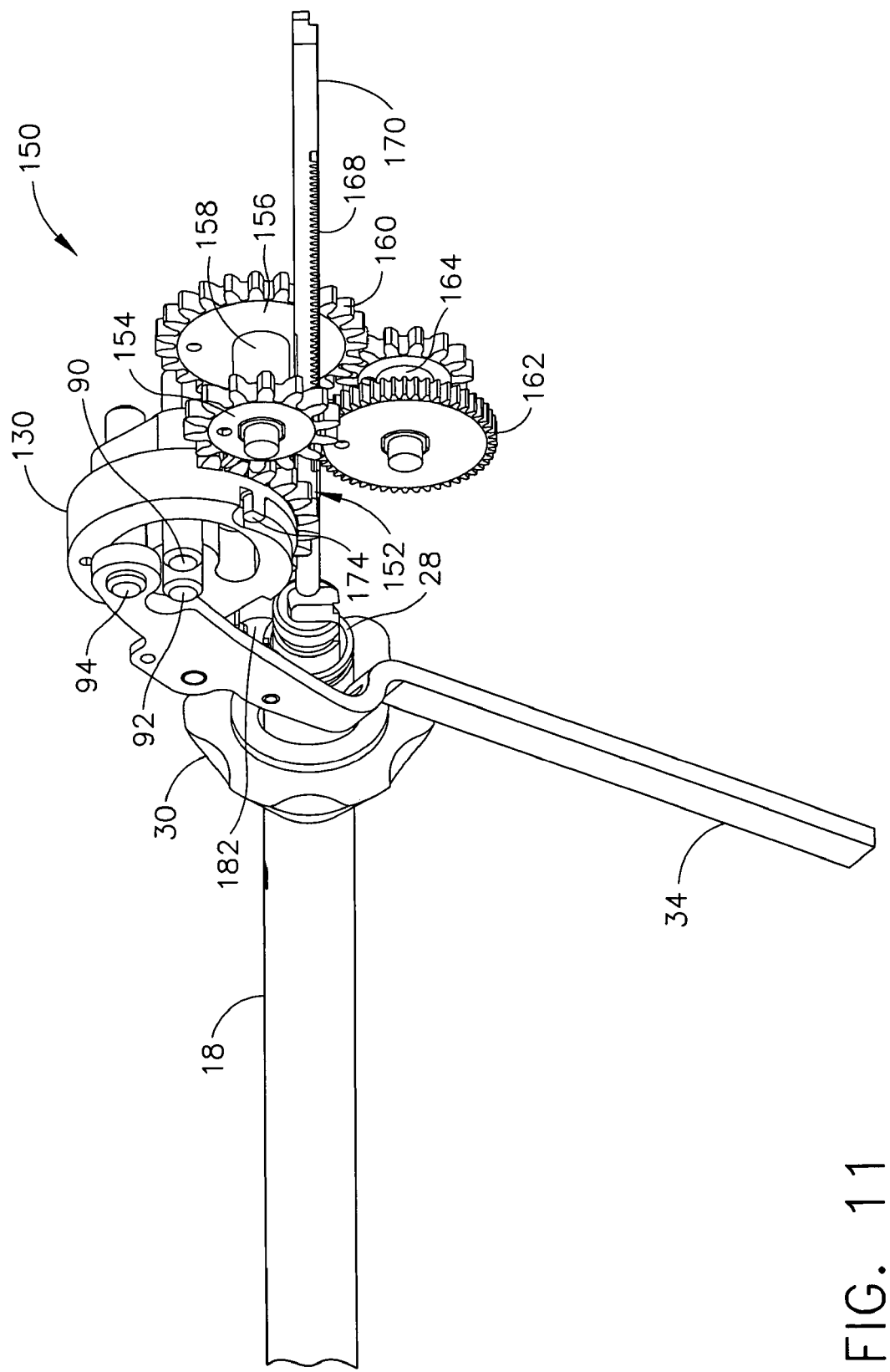
FIG. 11 is an aft perspective view of a rotary transmission firing mechanism of the handle of FIG. 1.

With particular reference to FIGS. 5, 9, 11, below and distal to the upper end 128 of the firing trigger 34 is a drive wedge pin hole 180 and a proximal pin hole 190. Drive wedge pin 184 and pin 196 extend inwardly from holes 180 and 190 (respectively) in firing trigger 34. Drive wedge 182 and a standoff finger 186 are pivotally mounted on drive wedge pin 184 and operably connected by a mousetrap-style spring 188. An opposing tension spring 194 between drive wedge 182 and pin 196 urge the drive wedge 182, standoff finger 186, and spring 188 clockwise (FIG. 10). When firing trigger 34 is actuated (FIG. 9), standoff finger 186 is brought into contact with a center, uncammed circumferential surface of the cam disk 120, rotating the standoff finger 186, spring 188 and drive wedge 182 counterclockwise. The counterclockwise motion of standoff finger 186 biases drive wedge 182 into firing engagement with the cam lobes 142-144 (FIG. 9).

Figure 12:
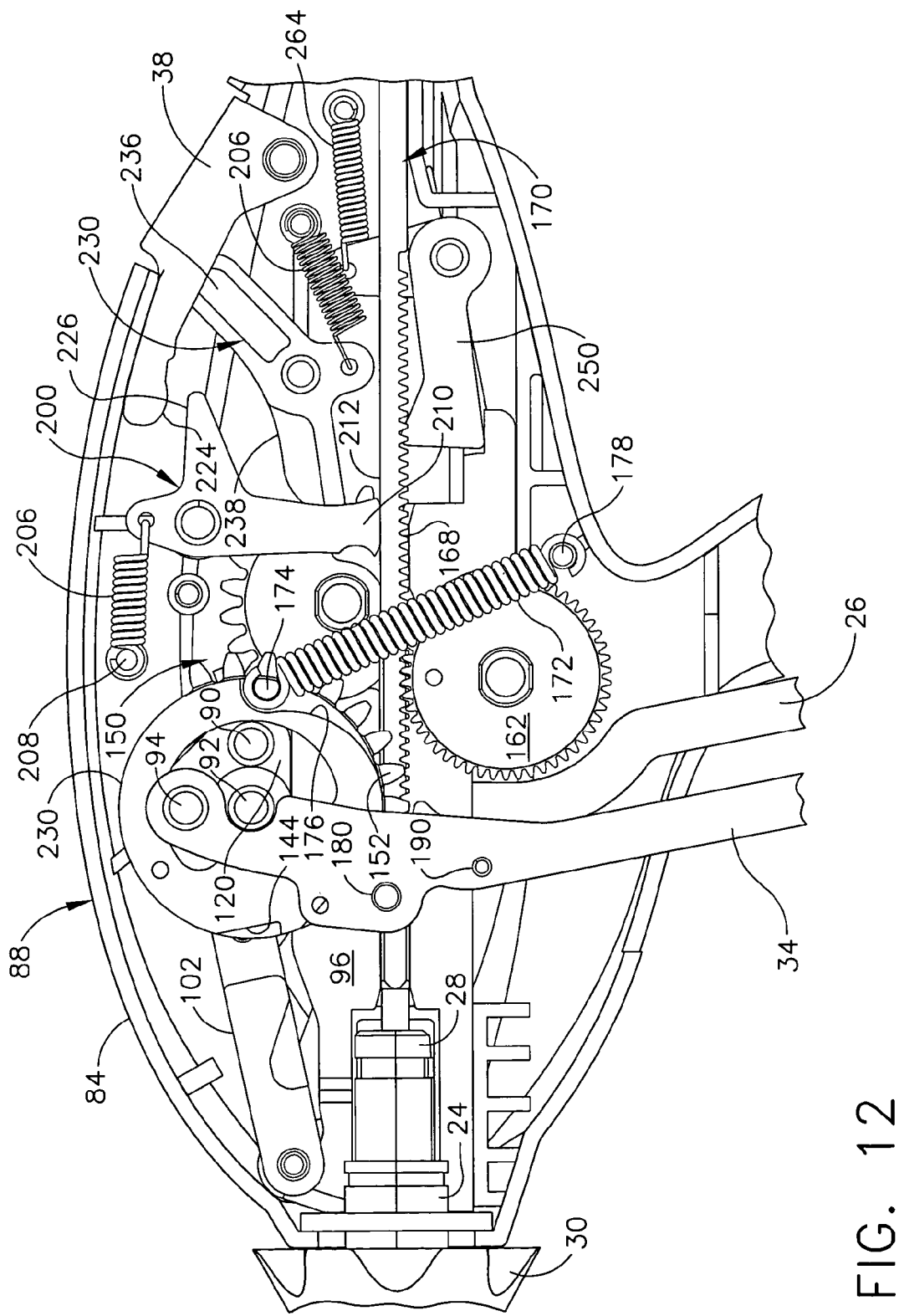
FIG. 12 is a side elevation view of the handle of FIG. 6 in a closed and fired condition with a small idler gear of the rotary transmission firing mechanism omitted to expose an anti-backup pendulum contacting a solid rack.

With particular reference to FIG. 12, when the drive wedge 182 is drawn away from one of the cam lobes 142-144 between firing strokes, the cam disk 130 would tend to rotate top to the rear by the action of the gear train retraction spring 172 but for the action of an anti-backup lever 200. Lateral pins 202, 204 of the anti-backup pendulum 200 engage respective right and left shell halves 84, 86 of the handle housing 88. Above the pins 202, 204, an anti-backup tension spring 206 is attached to an integral pin 208 of the right half shell 88 distal to the anti-backup pendulum 200. With particular reference to FIG. 5, a lower foot 210 of the anti-backup pendulum 200 makes frictional contact with an upper surface 212 of the solid rack 170. When the lower foot 210 of the anti-backup pendulum 200 is drawn proximally by a retracting solid rack 170, the anti-backup lever 20 approaches a perpendicular engagement to the solid rack 170 that increases the frictional force, locking the solid rack 170, which is sufficient to overcome the backdriving force provided by the gear train retraction spring 172. When the solid rack 170 is driven distally by the firing trigger 34, the lower foot 210 is pushed distally, reducing the friction and allowing firing. Excessive forward movement of the lower foot 210 is prevented by the idler axle 158 and by the urging from the anti-backup tension spring 206.

Figure 6:
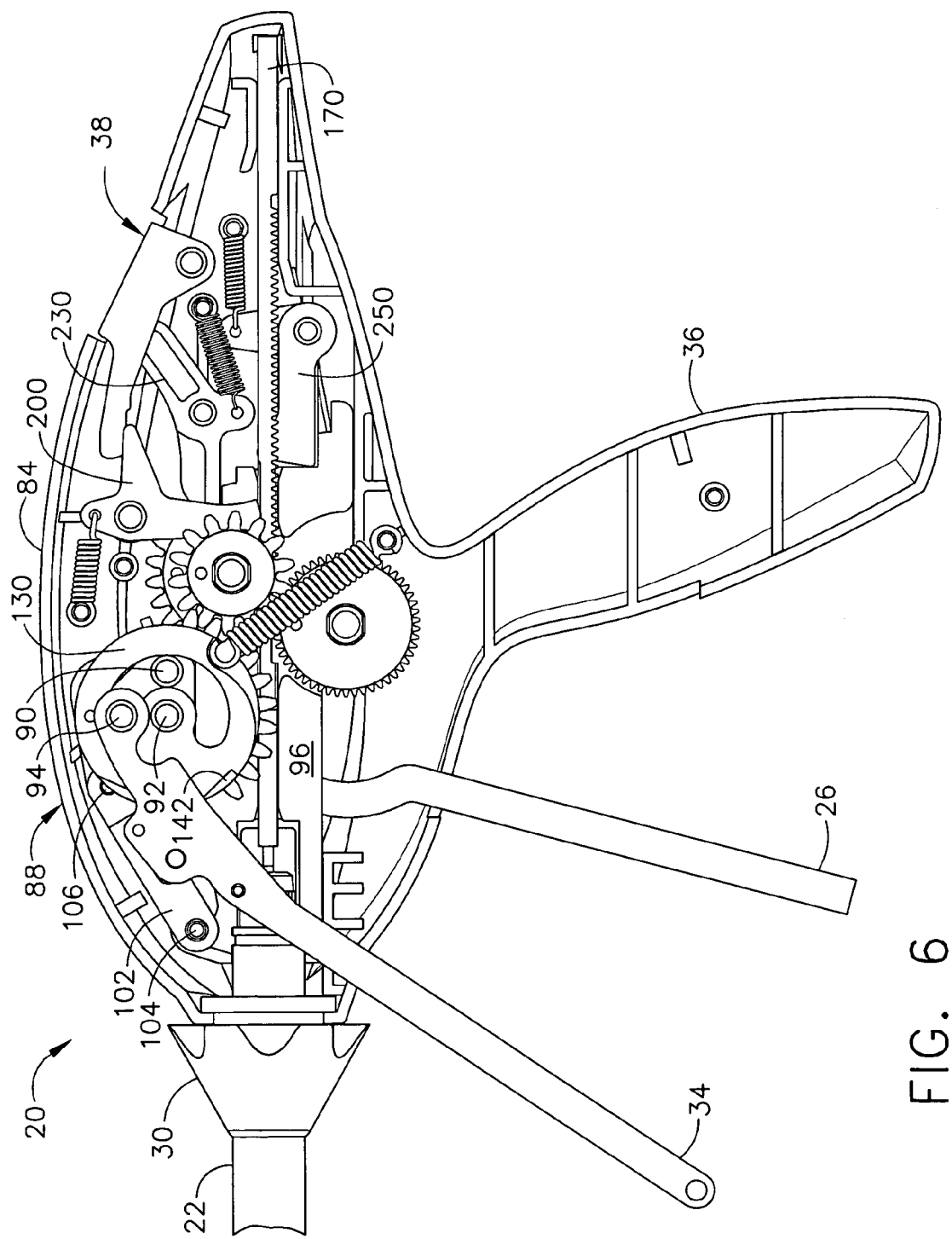
FIG. 6 is a left side view in elevation of the handle of the surgical stapling and severing instrument of FIG. 1 in an open condition with a left portion of a handle housing removed to expose a firing mechanism including a rotary transmission for multiple firing strokes.
Figure 7:
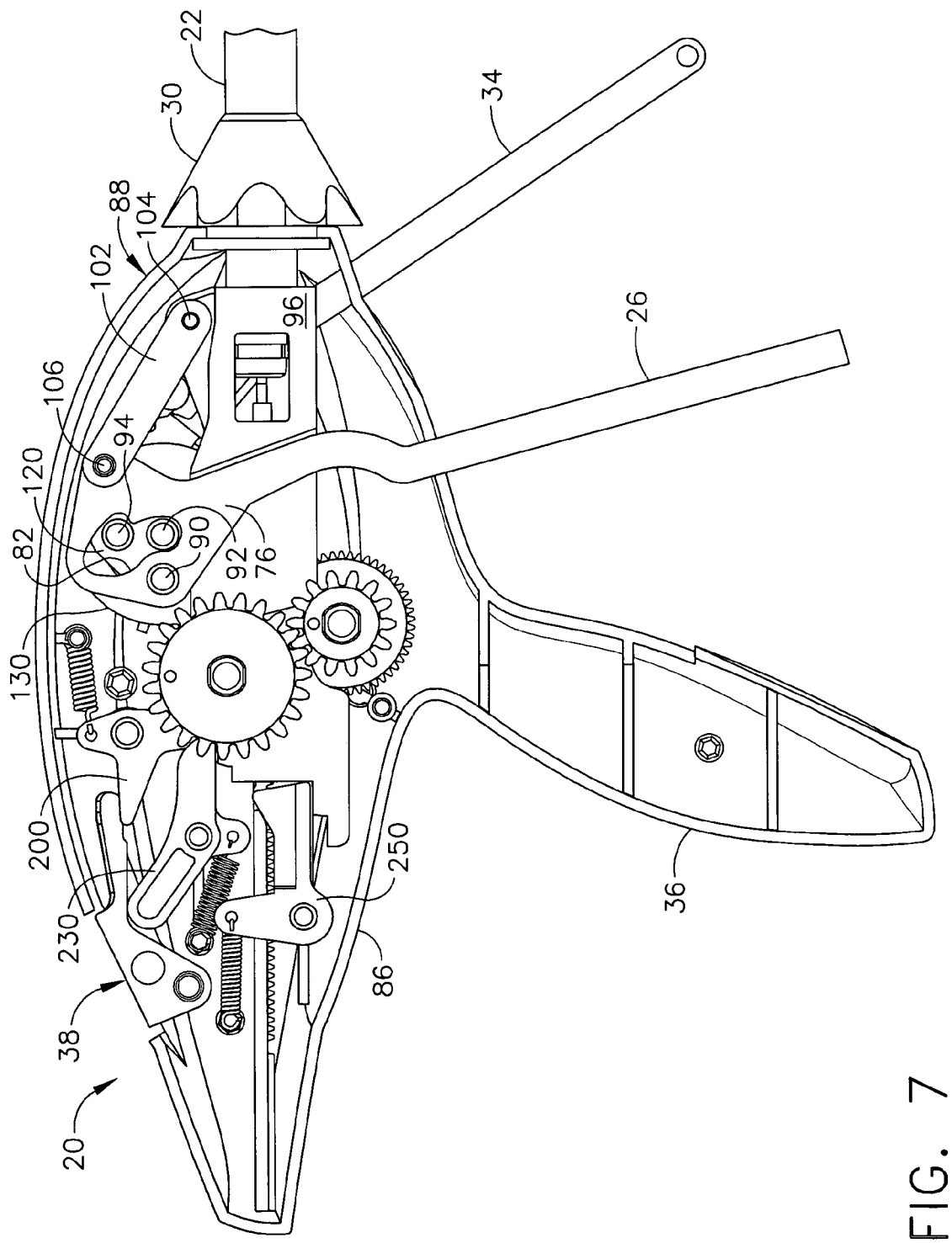
FIG. 7 is a right side view in elevation of the handle of FIG. 6 with a right portion of the handle portion removed to expose a closure mechanism and anti-backup features.
Figure 8:
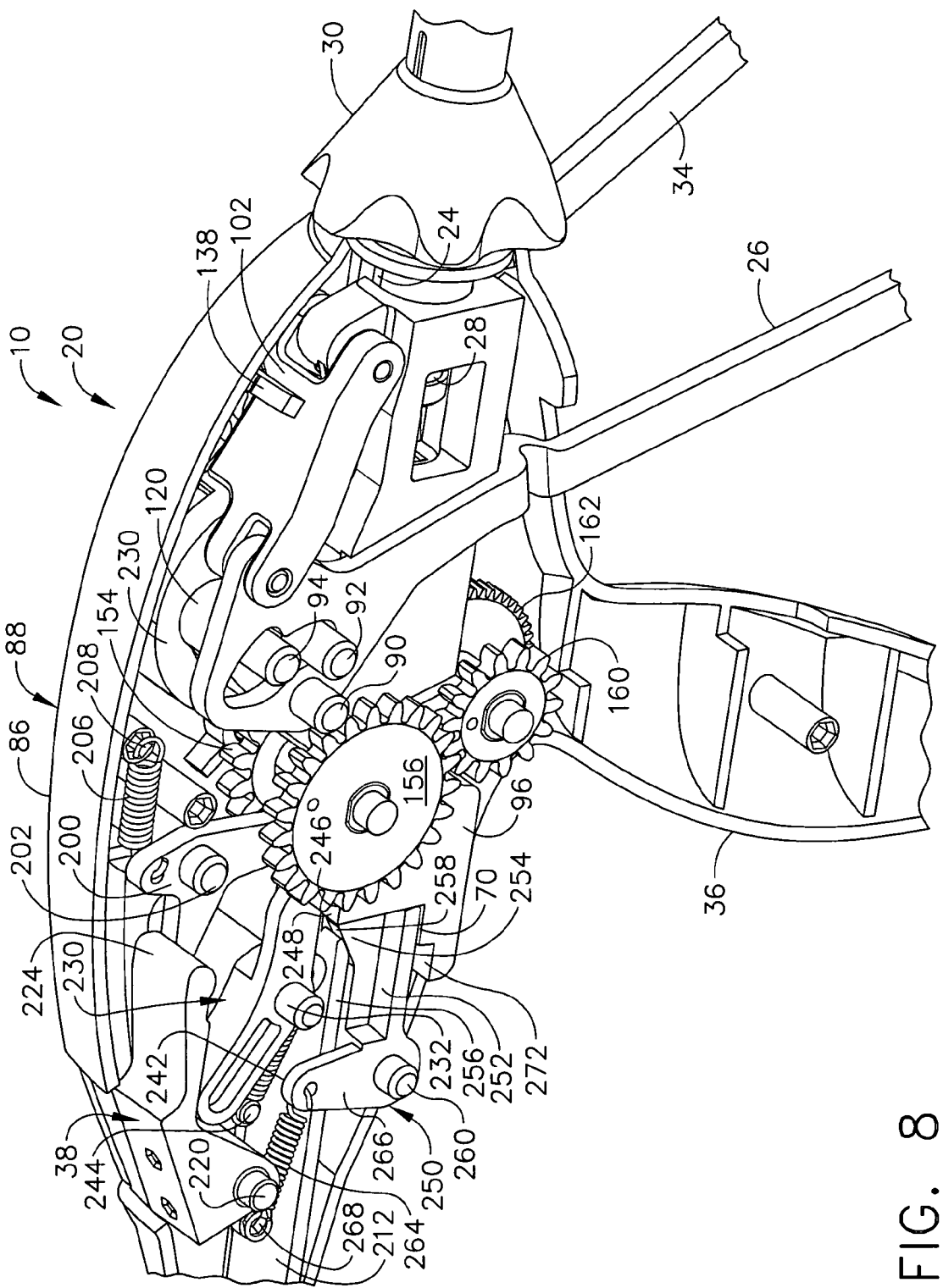
FIG. 8 is a downward perspective view of the handle of FIG. 7.

In FIG. 12, the release button 38 is pivoted upward about its aft pivot pins 220, 222, raising its distal arm 224 above a proximally directed arm 226 of the anti-backup pendulum 200 allowing distal movement of the lower foot 210 for locking the rack 170 between firing strokes. A clamp locking lever 230 rocks about its lateral pivot pins 232, 234 to effect this raising of the release button 38. In particular, a proximally and upwardly projecting arm 236 of the clamp locking lever 230 slidingly abuts an undersurface of the distal arm 224 of the release button 38. A distally projecting locking arm 238 of the clamp locking lever 230 locks the closure yoke 96 in its clamped condition. In particular, a tab 240 extending down between the proximally and upwardly projecting arm 236 and the distally projecting locking arm 238 is urged proximally by a tension spring 242 that is also attached to the right half shell 84 of the handle housing 88 at a pin 244. With reference to FIGS. 6-7, the distally projecting locking arm 238 rests upon a step 246 presented on a top, proximal portion of the closure yoke 96, allowing the closure yoke 96 to be distally moved to transfer the closure motion. A clamp locking notch 248, which is a distally and upwardly open recess of the step 246, receives the distally projecting locking arm 238 when the closure yoke 96 reaches its distal actuated position (FIG. 8, 9). Thus, the surgeon may release the closure trigger 26 with the end effector 12 remaining clamped.

With reference to FIGS. 5-8, 12, in addition to the afore-described anti-backup feature and closure clamping feature, a firing lockout feature is provided by a firing lockout lever 250. With the surgical stapling and severing instrument 10 in its initial open and unfired state, the firing lockout lever 250 responds to the closure yoke 96 being retracted by blocking distal, firing movement of the solid rack 170, as shown particularly in FIGS. 7 and 8. The firing lockout lever 250 includes a distally extending arm 252 having a distally ramped upper surface 254 that is aligned with a right edge 256 along the proximal portion of the solid rack 170. A recessed right edge 258 along the remaining distal portion of the solid rack 170 allows the distally ramped upper surface 254 of the firing lockout lever 250 to rotate upward, pivoting about its proximal lateral pins 260, 262 urged by a tension spring 264 connected to a vertical tab 266 that is perpendicularly and proximally attached to the distally extending arm 252. The other end of the tension spring 264 is connected to an integral pin 268 formed in the right half shell 84 of the handle housing 88 aft of the vertical tab 266.

As shown in FIG. 8, the distally ramped surface 254 blocks distal movement of the solid rack 170 by being wedged upward by a step 270 formed across the proximal end of the closure yoke 96, open proximally and upwardly to receive the downwardly pivoting distally extending arm 252 of the firing lockout lever 250. With the closure yoke 96 moved distally to close the end effector 12 as shown in FIG. 12, the right edge 256 of the solid rack 170 is allowed to pass over the distally ramped surface 254 that responds thereto by moving the distally extending arm 252 downward to engage a lower step 272 formed in the closure yoke 96 proximal to the higher and more distal step 270. The engagement of the firing lockout lever 250 to the lower step 272 has a benefit of preventing retraction (proximal movement) of the closure yoke 96 until the solid rack 170 is fully retracted. Thus, initiating retraction of the firing mechanism 42 advantageously occurs prior to unclamping of the end effector 12, which may otherwise cause binding in the firing mechanism 42. Moreover, enough frictional contact may exist between the lower step 272 and the firing lockout lever 250 to advantageously require a two-step procedure to return the surgical stapling and severing instrument 10 to its open and retracted condition. In particular, once the firing mechanism 42 has been retracted by depressing the release button 38, a slight squeeze on the closure trigger 26 would tend to allow the firing lockout lever 250 to raise to its firing lockout position. Thereafter, the release of the closure trigger 26 may proceed with the firing lockout lever 250 aligned for engagement of the higher step 270 when the closure yoke 96 is fully retracted and thus the end effector 12 opened.

It should further be appreciated that the rack 170 may be advantageously formed of links that allow a portion proximal to the firing mechanism 42 to be curved into the handle, allowing for a more compact design. Such a linked rack is described in greater detail in co-owned "SURGICAL STAPLING INSTRUMENT INCORPORATING A FIRING MECHANISM HAVING A LINKED RACK TRANSMISSION", Ser. No. 10/673,930, to Jeffrey S. Swayze, Frederick E. Shelton IV, filed 29 Sep. 2003, which is incorporated herein by reference in its entirety.

In use, the surgeon positions the end effector 12 and shaft 18 through the cannula of a trocar to a surgical site, positions the anvil 14 and elongate channel 16 as opposing jaws to grasp tissue to be stapled and severed. Once satisfied with the position of end effector 12, the closure trigger 26 is fully depressed toward the pistol grip 36 of the handle 20, causing a closure link 102 to advance a closure yoke 96 and thus a closure tube 24 to close the end effector 12. The distally moved closure yoke 96 presents a clamp locking notch 248 that receives a clamp locking lever 230, clamping the end effector 12. Stroking the firing trigger 34 multiple times effects firing of the firing rod 32 by sequentially engaging a drive wedge 182 that is coupled to the firing trigger 34 to cam lobes 142-144 on the cam disk 130. This ratcheting rotation is transferred through the rotary transmission firing mechanism 150 to distally advance the solid rack 170. With the closure yoke 96 advanced, the rack 170 is able to depress a firing lockout lever 250 out of the way. Between firing strokes, the anti-backup pendulum 100 is drawn into a perpendicular locking contact with the rack 170, opposing a retraction force imparted by the cam gear train retraction spring 172 connected to the cam gear 130. Once full firing travel is achieved, depressing the closure release lever 40 first disengages the anti-backup pendulum 100, allowing the solid rack 170 to retract and secondly disengages the clamp locking lever 230 from the closure yoke 96 to remove one impediment from opening the end effector 12. The surgeon squeezes the closure yoke 26 to allow the firing lockout lever 250 to release from the closure yoke 96 and releases the closure trigger 26, allowing the closure yoke 96 to proximally move to where it holds up the firing lockout lever 250 to lock out the sold rock 170 from firing. Thereafter, the implement portion 22 of the surgical stapling and severing instrument 10 may be removed such as for replacing the staple cartridge 62 in preparation for another operation.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

It will be appreciated that the terms "proximal" and "distal" are used herein with reference to a clinician gripping a handle of an instrument. Thus, the end effector 12 is distal with respect to the more proximal handle 20. It will be further appreciated that for convenience and clarity, spatial terms such as "vertical" and "horizontal" are used herein with respect to the drawings. However, surgical instruments are used in many orientations and positions, and these terms are not intended to be limiting and absolute.

The present invention is being discussed in terms of endoscopic procedures and apparatus. However, use herein of terms such as "endoscopic", should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures.

For instance, while a surgical stapling and severing instrument 10 is described herein that advantageously has separate and distinct closing and firing actuations, it should be appreciated that applications consistent with the present invention may include a handle that converts a single user actuation into a firing motion that closes and fires the instrument.

In addition, while a manually actuated handle is illustrated, a motorized or otherwise powered handle may benefit from incorporating a linked rack as described herein, allowing reduction of the size of the handle or other benefits. For instance, while partially stowing the linked rack into the pistol grip is convenient, it should be appreciated that the pivot connection between links allows for stowing the link parallel to the straight portion defined by the shaft and the barrel of the handle.

What is claimed is:
1. A surgical instrument, comprising:
an end effector operably configured to respond to a firing motion;
a shaft attached to the end effector and including an elongate firing member coupled to the end effector for movement to longitudinally transmit the firing motion; and
a handle proximally attached to the shaft, comprising:
a cam disk including a plurality of cam lobes about at least a portion of a circumference,
a firing actuator repeatably moveable in a firing direction and a return direction;

a wedge coupled to the firing actuator and operably configured to sequentially engage a respective one of the plurality of cam lobes of the cam disk during each movement of the firing actuator in the firing direction;

a rack connected to the firing member of the shaft and coupled by gear engagement with the cam disk to transmit an intermittent rotation of the cam disk as the longitudinal firing motion.

2. The surgical instrument of claim 1, wherein the rack is coupled by gear engagement with the cam disk comprised of a gear train.

3. The surgical instrument of claim 2, wherein the gear train comprises a gear reduction assembly relating the intermittent rotation of the cam disk to an increased longitudinal motion of the rack.

4. The surgical instrument of claim 1, further comprising an anti-backup mechanism operably configured to prevent retraction of the rack between firing strokes of the firing trigger.

5. The surgical instrument of claim 1, wherein the end effector comprises a pair of opposing jaws responsive to a closure motion and a firing bar responsive to the firing member, the shaft operably configured to transmit the closure motion through a closure member to the end effector, the handle further comprising a closure mechanism operably configured to produce the closure motion.

6. The surgical instrument of claim 5, further comprising a firing lockout mechanism responsive to the closure mechanism being unclosed to prevent movement of the rack.

7. The surgical instrument of claim 6, wherein the firing lockout mechanism is operably configured to respond to the rack having been at least partially fired to block opening movement of the closure mechanism.

8. The surgical instrument of claim 7, wherein the handle further comprises a clamp lock responsive to closure motion of the closure mechanism to lock the closure mechanism.

9. The surgical instrument of claim 5, wherein the handle further comprises:

a firing lockout mechanism responsive to the closure mechanism being unclosed to prevent movement of the rack and responsive to the rack being at least partially fired to prevent opening of the closure mechanism;

a clamp lock mechanism responsive to closure motion of the closure mechanism to lock the closure mechanism;

an anti-backup mechanism operably configured to prevent retraction of the rack between firing strokes of the firing trigger; and a release mechanism operably configured to unlock the anti-backup mechanism.

10. The surgical instrument of claim 9, wherein the release mechanism is further operably configured to unlock the clamp lock mechanism.

11. The surgical instrument of claim 5, wherein the end effector is operably configured to staple and sever tissue during firing.

12. The surgical instrument of claim 1, wherein the handle further comprises a pistol grip, the rack comprises a bendable rack stowable in the pistol grip when retracted.

13. A surgical instrument, comprising:

an end effector operably configured to respond to a firing motion;

a shaft attached to the end effector and including an elongate firing member coupled to the end effector for movement to longitudinally transmit the firing motion; and a handle proximally attached to the shaft, comprising:

a firing actuator repeatably moveable in a firing direction and a return direction, a rack connected to the firing member of the shaft, and a means for rotationally coupling repeated firing direction motion from the firing actuator into the rack and maintaining a current position of the rack during return direction motion of the firing actuator.

14. The surgical instrument of claim 13, wherein the end effector further comprises a stapling and severing apparatus responsive to the firing motion.

15. The surgical instrument of claim 14, wherein the stapling and severing apparatus further comprises a pair of opposing jaws responsive to a closing motion, the handle further comprising a means for closing the pair of opposing jaws.

* * * * *